US006264993B1

(12) United States Patent
Young et al.

(10) Patent No.: US 6,264,993 B1

(45) Date of Patent: Jul. 24, 2001

(54) FUNGICIDAL COMPOSITIONS CONTAINING N-ACETONYLBENZAMIDES

(75) Inventors: David Hamilton Young, Ambler; Willie Joe Wilson, Chalfont; Anne Ritchie Egan; Enrique Luis Michelott, both of Fort Washington, all of PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/561,037

(22) Filed: Apr. 28, 2000

Related U.S. Application Data

(60) Continuation-in-part of application No. 09/433,676, filed on Nov. 4, 1999, now Pat. No. 6,075,047, which is a division of application No. 09/148,604, filed on Sep. 4, 1998, now Pat. No. 6,004,947

(60) Provisional application No. 60/072,725, filed on Jan. 27, 1998.

(51) Int. Cl.[7] ........................... A01N 59/26; A01N 37/18

(52) U.S. Cl. .......................... 424/605; 424/601; 514/617

(58) Field of Search ............................ 514/617; 424/605, 424/601

(56) References Cited

U.S. PATENT DOCUMENTS

| | | | |
|---|---|---|---|
| 5,304,572 | 4/1994 | Michelotti et al. | 514/514 |
| 5,677,333 | 10/1997 | Loughner et al. | 514/491 |

*Primary Examiner*—Allen J. Robinson
(74) *Attorney, Agent, or Firm*—Clark R. Carpenter

(57) ABSTRACT

The present invention relates to fungicidal compositions and their use as a method for controlling phytopathogenic fungi comprising the application of a selected fungicidally active N-acetonylbenzamide compound and a second fungicidally active compound selected from the group consisting of an inhibitor of respiration at cytochrome complex III, ziram, fluazinam, zarilamide, chlorothalonil, propamocarb, folpet, fosetyl-aluminum or a fungitoxic metabolite thereof, phosphorous acid or a salt thereof, a triphenyltin type fungicide and a copper containing fungicide to plant seed, to plant foliage or to a plant growth medium. The compositions and method of use provide higher fungicidal activity than separate use of the same compounds.

5 Claims, No Drawings

FUNGICIDAL COMPOSITIONS CONTAINING N-ACETONYLBENZAMIDES

This is a continuation-in-part application of pending Ser. No. 09/433,676, filed Nov. 4, 1999 now U.S. Pat. No. 6,075,047, Jun. 13, 2000) which is a divisional application of Ser No. 09/148,604, filed Sep. 4, 1998 (now U.S. Pat. No. 6,004,947, Dec. 21,1999) which claims for domestic priority 60/072,725 filed Jan. 27, 1998.

The present invention relates to new fungicidal compositions and their use as a method for controlling phytopathogenic fungi on plants.

It is always desirable to improve products which can be used by growers in order to combat fungal diseases of crops, and in particular diseases caused by fungi in the class Oomycetes.

It is also always desirable to reduce the doses of chemical products spread into the environment to combat fungal attacks on crops, in particular by reducing the application doses of the products.

It is also always desirable to increase the number of antifungal products available to growers in order that they will find, among these products, the one which is best suited to the grower's specific use.

One objective of the invention is thus to provide novel fungicidal compositions which are useful against the problems outlined above.

Another objective of the invention is to propose novel fungicidal compositions which are useful in the preventive and curative treatment of diseases caused by fungi of the class Oomycetes.

Still another objective of the invention is to propose novel fungicidal compositions which are of improved efficacy against mildew and/or late blight caused by Oomycetes.

Yet another objective of the invention is to propose novel fungicidal compositions which are of improved efficacy against downy mildew in grapes and other crops and/or late blight in tomatoes and potatoes.

It has now been found that these objectives may be achieved, partly or totally, by means of the fungicidal compositions according to the present invention.

U.S. Pat. Nos. 5,304,572 and 5,677,333 disclose applying mixtures of the N-acetonylbenzamides disclosed therein with other fungicidal compounds. It has now been discovered that application of the N-acetonylbenzamides disclosed in these patents in combination with selected other fungicidal compounds provides unexpectedly high fungicidal activity and is effective in controlling phytopathogenic fungi at lower N-acetonylbenzamide dosage rates than those disclosed in the U.S. Pat. No. 5,304,572 patent. Although U.S. Pat. No. 5,677,333 discloses the use of N-acetonylbenzamides in combination with ethylene bisdithiocarbamates, cymoxanil and dimethomorph to provide unexpectedly high fungicidal activity, the synergistic combinations of this invention are not disclosed or suggested in that patent.

In a first embodiment of this invention, there is provided a composition comprising (a) a fungicidally effective amount of a first fungicidally active compound having the formula (I)

(I)

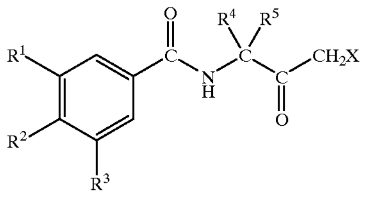

or an agronomically acceptable salt thereof wherein $R^1$ and $R^3$ are each independently halo or $(C_1-C_4)$ alkyl, $R^2$ is $(C_1-C_4)$alkyl, $(C_2-C_4)$alkenyl, $(C_2-C_6)$ alkynyl, $(C_1-C_4)$alkoxy or cyano, $R^4$ and $R^5$ are each independently a hydrogen atom or $(C_1-C_4)$alkyl, provided that at least one of $R^4$ and $R^5$ is $(C_2-C_4)$alkyl and X is halo, thiocyano or isothiocyano;

(b) a fungicidally effective amount of a second fungicidally active compound elected from the group consisting of (i) an inhibitor of respiration at cytochrome complex III, such as a ethoxyacrylate type fungicide, for example, azoxystrobin and kresoxim-methyl, (ii) ziram (iii) fluazinam (iv) zarilamide (v) chlorothalonil (vi) propamocarb (vii) folpet (viii) fosetyl-aluminum or a fungitoxic metabolite thereof such as phosphorous acid, or a salt of phosphorous acid such as potassium, (ix) a triphenyltin type fungicide such as fentin hydroxide and fentin acetate and (x) a copper containing fungicide such as copper(I) sulfate, copper(II) sulfate, copper(II) sulfate pentahydrate, copper(I) oxide and Bordeaux mixture; and (c) an agronomically acceptable carrier.

In a second embodiment of this invention, there is provided a method for controlling phytopathogenic fungi on a plant comprising the application of (a) a fungicidally effective amount of a first fungicidally active compound having the formula (I)

(I)

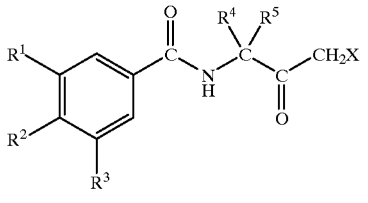

or an agronomically acceptable salt thereof wherein $R^1$ and $R^3$ are each independently halo or $(C_1-C_4)$ alkyl, $R^2$ is $(C_1-C_4)$alkyl, $(C_2-C_4)$alkenyl, $(C_2-C_6)$ alkynyl, $(C_1-C_4)$alkoxy or cyano, $R^4$ and $R^5$ are each independently a hydrogen atom or $(C_1-C_4)$alkyl, provided that at least one of $R^4$ and $R^5$ is $(C_2-C_4)$alkyl and X is halo, thiocyano or isothiocyano;

(b) a fungicidally effective amount of a second fungicidally active compound selected from the group consisting of (i) an inhibitor of respiration at cytochrome complex III, such as a methoxyacrylate type fungicide, for example, azoxystrobin and kresoxim-methyl, (ii) ziram (iii) fluazinam (iv) zarilamide (v) chlorothalonil (vi) propamocarb (vii) folpet (viii) fosetyl-aluminum or a fungitoxic metabolite thereof such as phosphorous acid, or a salt of phosphorous acid such as potassium, (ix) a triphenyltin type fungicide such as fentin hydroxide and fentin acetate and (x) a copper containing fungicide such as copper(I) sulfate, copper(II) sulfate, copper(II) sulfate pentahydrate, copper(I) oxide and Bordeaux mixture; and (c) an agronomically acceptable carrier to the plant seed, to the plant foliage or to the growth medium for the plant.

When $R^4$ and $R^5$ are different, optical enantiomers of the compounds of the present invention are possible due to the presence of an asymmetric carbon atom linking $R^4$ and $R^5$. It is known that many biologically active compounds have optical enantiomers, one of which is more active than the other. Similarly, for compounds used in the method of the present invention, the biological activity of one enantiomer may exceed that of the other enantiomer, as described in "$(C_1-C_4)$alkyl" means a straight or branched alkyl group having one to four carbon atoms per group and includes methyl, ethyl, n-propyl, isopropyl, n-butyl, isobutyl, sec-butyl and tert-butyl.

"$(C_2-C_4)$alkenyl" means a straight or branched alkenyl group having two to four carbon atoms per group and includes, for example, ethenyl, 2-propenyl, 2-butenyl, 1-methylethenyl, 2-methyl-2-propenyl and the like.

"$(C_2-C_6)$alkynyl" means a straight or branched alkynyl group having from two to six carbons per group and includes, for example, ethynyl, 2-propynyl, 2-butynyl and the like.

"Halo" means chloro, fluoro, bromo and iodo.

"$(C_1-C_4)$alkoxy" means a straight or branched alkoxy group having one to four carbon atoms per group and includes, for example, methoxy, ethoxy, n-propoxy, isopropoxy, n-butoxy, isobutoxy, sec-butoxy and tert-butoxy.

"Cyano" means a group having the structural formula —CN.

"Thiocyano" means a group having the structural formula —SCN.

"Isothiocyano" means a group having the structural formula —NCS.

Agronomically acceptable salts include, for example, metal salts such as sodium, potassium, calcium and magnesium salts, ammonium salts such as isopropyl ammonium salts and trialkylsulfonium salts such as triethylsulfonium salts.

The first fungicidally active compound may be a single compound of formula (I) or, alternatively, may be a mixture of compounds of formula (I). Suitable compounds of formula (I) include, but are not limited to, N-[3'-(1'-chloro-3'-methyl-2'-oxopentan)]-3,5-dichloro-4-methylbenzamide, N-[3'-(1'-chloro-3'-methyl-2'-oxopentan)]-3,5-dichloro-4-ethylbenzamide, N-[3'-(1'-chloro-3'-methyl-2'-oxopentan)]-3,5-dichloro-4-ethoxybenzamide, N-[3'-(1'-chloro-3'-methyl-2'-oxopentan)]-3,5-dichloro-4-methoxybenzamide, N-[3'-(1'-chloro-3'-methyl-2'-oxopentan)]-3,5-dichloro-4-cyanobenzamiide, and N-[3'-(1'-chloro-3'-methyl-2'-oxopentan)]-3,5-dibromo-4-methylbenzamide.

In a preferred embodiment, the first fungicidally active compound is

N-[3'-(1'-chloro-3'-methyl-2'-oxopentan)]-3,5-dichloro-4-methylbenzamide,

N-[3'-(1'-chloro-3'-methyl-2'-oxopentan)]-3,5-dibromo-4-cyanobenzamide or mixture thereof.

More preferably, the first fungicidally active compound is

N-[3'-(1'-chloro-3'-methyl-2'-oxopentan)]-3,5-dichloro-4-methylbenzamide.

Suitable compounds which function as the second fungicidally active compound include, but are not limited to, azoxystrobin, kresoxim-methyl, ziram, fluazinam, zarilamide, chlorothalonil, propamocarb, folpet, fosetyl-aluminum, phosphorous acid or the potassium salt of phosphorous acid, fentin hydroxide, fentin acetate, copper(l) sulfate, copper(II) sulfate, copper(II) sulfate pentahydrate, copper(I) oxide and Bordeaux mixture.

In a preferred embodiment, the second fungicidally active compound is selected from the group consisting of fluazinam, propamocarb, folpet, fosetyl-aluminum, phosphorous acid or the potassium salt of phosphorous acid, and copper(II) sulfate pentahydrate.

The method of the present invention may optionally further comprise application of other compounds having biological activity, for example, additional fungicidally active compounds or compounds having herbicidal activity or insecticidal activity, to the plant seed, to the plant foliage or to the growth medium for the plant.

The method of the present invention is useful for the control of phytopathogenic fungi on crops and the first and second fungicidally active compounds may be applied as a soil fungicide, as a seed protectant, as a foliar fungicide or as a combination thereof In a preferred embodiment, the first and second fungicidally active compounds are applied to a plant growth medium, to the plant seed or to plant foliage at dosage rates of from 2 parts by weight (pbw) to 90 pbw, more preferably from 5 pbw to 75 pbw, of the first fungicidally active compound per 100 pbw of the combined amount of first and second fungicidally active compounds and from 10 pbw to 98 pbw, more preferably from 25 pbw to 95 pbw, of the second fungicidally active compound per 100 pbw of the combined amount of first and second fungicidally active compounds.

As a soil fungicide, the first and second fungicidally active compositions can be incorporated in the soil or applied to the surface of the soil at a dosage rate of about 0.25 kg to 5 kg of the first fungicidally active compound and from 0.25 kg to 5 kg of the second fungicidally active compound per hectare As a seed protectant, the first and second fungicidally active compounds are coated on seed at a dosage rate of about 0.5 kilograms (kg) to 5 kg of the first fungicidally active compound and from 0.5 kg to 5 kg of the second fungicidally active compound per 100 kg seed.

As a foliar fungicide, the first and second fungicidally active compounds are applied to plant foliage at a dosage rate of from 0.01 kg per hectare to 5 kg per hectare of the first fungicidally active compound, and a dosage rate of from 0.01 kg per hectare to about 5 kg per hectare of the second fungicidally active compound. In a preferred embodiment, the first fungicidally active compound is applied to plant foliage at a dosage rate of from 0.05 kg per hectare to about 0.5 kg per hectare. In a preferred embodiment, the second fungicidally active compound is applied to plant foliage at a dosage rate of 0.05 kg per hectare to 5.0 kg per hectare. The first and second fungicidally active compounds can be applied to plant foliage as fungicidal sprays by methods commonly employed, such as conventional high-gallonage hydraulic sprays, low-gallonage sprays, air-blast, aerial sprays and dusts. While the dilution and rate of application will depend upon the type of equipment employed, the method and frequency of application desired and diseases to be controlled, the effective amount is typically from about 0.1 kg to about 5.0 kg, preferably 0.2 kg to 5.0 kg, of both the first and second active compounds per hectare.

The first and second fungicidally active compounds may be applied simultaneously or sequentially.

In a preferred embodiment, the first and second fungicidally active compounds are simultaneously applied to plant growth medium, the plant seed, plant foliage or a combination thereof as a composition comprising a mixture of the first fungicidally active compound and second fungicidally active compound. In the preferred embodiments, the mixture includes from 2 pbw to 90 pbw of a first fungicidally active compound and from 10 pbw to 98 pbw of a second fungicidally active compound per 100 pbw of the mixture.

In an alternative embodiment, the first and second fungicidally active compounds are applied sequentially to the plant seed, plant foliage or plant growth medium, with application of the second-applied compound following application of the first-applied compound by up to 72 hours. The compounds may be applied in either order: either the first fungicidally active compound followed by the second fungicidally active compound or, alternatively, as application of the second fungicidally active compound followed by the first fungicidally active compound.

The method of the present invention is useful in controlling certain phytopathogenic fungi, particularly fungi of the class Oomycetes, and provides high fungicidal activity and relatively low phytotoxicity. The method of the present invention is particularly effective in controlling Oornycete fungi of the genera Phytophthora, Plasmopara, Peronospora, Albugo and Pseudoperonospora, and even more particularly against the organisms of those genera that cause diseases such as late blight in tomatoes and potatoes and downy mildew in grapes and other crops, including, for example, *Phytophthora infestans, Plasynopara viticola* and *Pseudoperonospora cubensis.*

For each of the above disclosed purposes, the first and second fungicidally active compounds can be used in the technical or pure form as prepared, as solutions or as formulations. The compounds are usually taken up in a carrier or are formulated so as to render them suitable for subsequent use as fungicides. For example, the compounds can be formulated as wettable powders, dry powders, emulsifiable concentrates, dusts, granular formulations, aerosols, or flowable emulsion concentrates. In such formulations, the compounds are extended with a liquid or solid carrier and, when dried, suitable surfactants are incorporated. It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in McCutcheon's "Emulsifiers and Detergents", McCutcheon's "Emulsifiers and Detergents/Functional Materials" and McCutcheon's "Functional Materials" all published annually by McCutcheon Division of MC Publishing Company (New Jersey).

In general, the compositions utilized in this invention can be dissolved in appropriate solvents such as acetone, methanol, ethanol, dimethylformamide or dimethyl sulfoxide and such solutions extended with water. The concentrations of the combined first and second active compounds in the solution can vary from 1% to 90% with a preferred range being 5% to 50%.

For the preparation of emulsifiable concentrates, the compositions used in the invention can be dissolved in suitable organic solvents or a mixture of solvents, together with an emulsifying agent which permits dispersion of the first and second active compounds in water. The concentration of the combined first and second active compounds in emulsifiable concentrates is usually 10% to 90% and in flowable emulsion concentrates, this can be as high as 75%. Wettable powders suitable for spraying, can be prepared by admixing the composition with a finely divided solid, such as clays, inorganic silicates and carbonates, and silicas and incorporating wetting agents, sticking agents, and/or dispersing agents in such mixtures. The concentration of the combined first and second active compounds in such formulations is usually in the range of 20% to 98%, preferably 40% to 75%.

Dusts are prepared by mixing the composition of the present invention, or salts and complexes thereof, with finely divided inert solids which can be organic or inorganic in nature. Inert materials useful for this purpose include botanical flours, silicas, silicates, carbonates and clays. One convenient method of preparing a dust is to dilute a wettable powder with a finely divided carrier. Dust concentrations containing 20% to 80% of the combined first and second active compounds are commonly made and are subsequently diluted to 1% to 10% use concentration.

The method of the present invention, wherein an N-acetonylbenzamide and a selected second fungicidally active compound are applied to plant seed, plant foliage or to a plant growth medium, unexpectedly provides higher fungicidal activity than the same compounds used separately.

The results provided by the mixtures were compared with the predicted results that were calculated using the formula set forth by S. R. Colby in *Weeds* 1967, 15, 20–22 ("Colby's Formula") from the results obtained using each of the compounds individually. The predicted results are also provided in the following Examples. These examples, tables and experimental procedures are provided for guidance to the practitioner and are not meant to limit the scope of the invention which is defined by the claims.

EXAMPLE 1

Test to Control *Phytophthora capsici* Using N-[3'-(1'-chloro-3'-methyl-2'-oxopentan)]-3,5-dichloro-4-methylbenzarnide (Compound A) and Phosphorous Acid (Compound C)

A dilution series of Compound A was prepared in dimethylsulfoxide (DMSO) and a dilution series of Compound C was prepared in sterile water. Aliquots of each were added to 25 ml of molten potato dextrose agar at 50° C. to give the appropriate concentrations shown in the table below. Immediately after adding the compound(s), the molten agar was poured into 9 cm diameter petri plates and allowed to harden. The final concentration of DMSO in all plates was 0.25%. Control plates contained DMSO but neither compound. Plates were inoculated in the center with 1 μl of a suspension of *Phytophthora capsici* (ATCC 15399, obtainable from the American Type Culture Collection, Rockville, Md., U.S.A) zoospores containing $5\times10^5$ zoospores per milliliter. Three replicate plates were used for each treatment. Fungal colony diameters were measured after growth for 7 days at 25° C., and two measurements were taken from each plate. Inhibition of growth was calculated by comparing growth in the treatments with compound A and/or C with growth in the controls. Degree of inhibition (Observed) is expressed as a percentage in Table 1 below. The predicted % inhibition in treatments containing both A and C was calculated using the Colby Formula

TABLE 1

Control of *Phytophthora capsici*

| Compound A Concentration ppm | Compound C Concentration ppm | % Inhibition (Observed) | % Inhibition (Predicted) |
|---|---|---|---|
| 0 | 70 | 48.3 | |
| 0 | 100 | 72.1 | |
| 0.2 | 0 | 34.1 | |
| 0.3 | 0 | 52.8 | |
| 0.2 | 70 | 75.4 | 65.9 |
| 0.3 | 70 | 77.3 | 75.6 |
| 0.2 | 100 | 88.1 | 81.6 |
| 0.3 | 100 | 91.1 | 86.8 |

EXAMPLE 1A

In Vitro Test to Control *Phytophthora capsici* Using N-[3'-(1'chloro-3'-methyl-2'-oxopentan)]-3,5-dichloro-4-methylbenzamide (Compound A) and the Potassium salt of Phosphorous Acid (Compound C-1)

A dilution series of Compound A was prepared in dimethylsulfoxide (DMSO) and a dilution series of Compound C-1 was prepared in sterile water. Aliquots of each were added to 25 ml of molten potato dextrose agar at 50° C. to give the appropriate concentrations shown in the table below. Immediately after adding the compound(s), the molten agar was poured into 9-cm diameter petri plates and allowed to harden. The final concentration of DMSO in all plates was 0.25%. Control plates contained DMSO but neither compound. Plates were inoculated in the center with 1 μl of a suspension of *Phytophthora capsici* (ATCC 15399, obtainable from the American Type Culture Collection, Rockville, Md., U.S.A) zoospores containing $5\times10^5$ zoospores per milliliter. Three replicate plates were used for each treatment. Fungal colony diameters were measured after growth for 7 days at 25° C., and two measurements were taken from each plate. Inhibition of growth was calculated by comparing growth in the treatments with compound A and/or C-1 with growth in the controls. Degree of inhibition (Observed) is expressed as a percentage in Table 1A below. The predicted % inhibition in treatments containing both A and C-1 was calculated using the Colby Formula, which is known to those skilled in the art (R. S. Colby, *Weeds* 15, 20–22 (1967)).

TABLE 1A

Control of *Phytophthoru cavsici*

| Compound A Concentration ppm | Compound C-1 Concentration ppm | % Inhibition (Observed) | % Inhibition (Predicted) |
|---|---|---|---|
| 0 | 250 | 15.3 | |
| | 500 | 31.5 | |
| | 750 | 44.2 | |
| 0.04 | 0 | 27.6 | |
| 0.08 | 0 | 52.3 | |
| 0.12 | 0 | 54.9 | |
| 0.16 | 0 | 65.2 | |
| 0.04 | 250 | 53.9 | 38.7 |
| 0.08 | 250 | 68.8 | 59.6 |
| 0.12 | 250 | 74.1 | 61.8 |
| 0.16 | 250 | 83.2 | 70.5 |
| 0.04 | 500 | 63.2 | 50.4 |
| 0.08 | 500 | 77.9 | 67.3 |
| 0.12 | 500 | 84.4 | 69.1 |
| 0.16 | 500 | 85.4 | 76.2 |
| 0.04 | 750 | 77.9 | 59.6 |
| 0.08 | 750 | 81.0 | 73.4 |
| 0.12 | 750 | 87.2 | 74.8 |
| 0.16 | 750 | 88.5 | 80.6 |

EXAMPLE 2

Test to Control *Phytophthora capsici* Using N-[3'-(1'-chloro-3'-methyl-2'-oxopentan)]-3,5-dichloro-4-methylbenzamide (Compond A) and $CuSO_45H_2O$ (Compound D)

The test protocol followed was the same as described in Example 1 and the results reported in Table 2.

TABLE 2

Control of *Phytophthora capsici*

| Compound A Concentration ppm | Compound C-1 Concentration ppm | % Inhibition (Observed) | % Inhibition (Predicted) |
|---|---|---|---|
| 0 | 100 | 15.6 | |
| 0 | 200 | 47.0 | |
| 0 | 300 | 59.2 | |
| 0.1 | 0 | 21.6 | |
| 0.2 | 0 | 31.0 | |
| 0.3 | 0 | 44.0 | |
| 0.1 | 100 | 49.4 | |
| 0.2 | 100 | 60.9 | 41.8 |
| 0.3 | 100 | 68.3 | 52.7 |
| 0.1 | 200 | 84.7 | 58.4 |
| 0.2 | 200 | 98.6 | 63.4 |
| 0.3 | 200 | 100 | 70.3 |
| 0.1 | 300 | 100 | 68.0 |
| 0.2 | 300 | 100 | 71.8 |
| 0.3 | 300 | 100 | 77.2 |

EXAMPLE 3

N-[3'-(1'-chloro-3'-methyl-2'-oxopentan)]-3,5-dichloro-4-5 methylbenzamide (Compound A)+ Fosetyl-aluminum (Compound E) Combination Study Two trials were conducted with the combination of fosetyl-aluminum and N-[1'-(1'-chloro-3'-methyl-2'-oxopentan)]-3,5-dichloro-4-methylbenzamide to evaluate the potential benefits of combinations of the two products.

The first trial was conducted to determine the appropriate rates for use in a combination of the two products.

Ratios where synergism was observed are 1:2.25, 1:4.5, 1:9, 1:18 and 1:36.

EXAMPLE 3a

N-[3'-(1'-chloro-3'-methyl-2'-oxopentan)]-3,5-dichloro-4-methylbenzamide+Fosetyl-aluminum Combination Study—Preliminary Application Rate Study Two to three week old Bush Champion cucumbers and 2 week old Patio tomatoes were sprayed with the fungicidal compounds as protectant sprays. The plants were inoculated with cucumber downy mildew (CDM), *Pseudoperonospora cubensis*, and tomato late blight (TLB), *Phytophthora infestans*, one day after spraying.

N-[3'-(1'-chloro-3'-methyl-2'-oxopentan)]-3,5-dichloro-4-methylbenzamide was extremely effective against the tomato late blight fungus in this test. N-[3'-(1'-chloro-3'-methyl-2'-oxopentan)]-3,5-dichloro-4-methylbenzamide alone at all rates tested gave 95% control or better. Since excellent results were observed with N-[3'-(1'-chloro-3'-methyl-2'-oxopentan)]-3,5-dichloro-4-methylbenzamide at the rates tested, no synergism could be detected.

Cucumber downy mildew control with N-[3'-(1'-chloro-3'-methyl-2'-oxopentan)]-3,5-dichloro-4-methylbenzamide ranged from 63 to 82%. There was a suggestion of synergism at some rates. The data suggested that the N-[3'-(1'-chloro-3'-methyl-2'-oxopentan)]-3,5-dichloro-4-methylbenzamide rates should be lowered and the trial repeated.

Using the Colby equation, E=X+Y−XY/100, results suggest that ratios or 1:2.25 to 1:4.5 were potentially synergistic. The results of the calculations are recorded in CDM calc. column as shown in Table 3a.

TABLE 3a

Control of CDM and TLB

| Treatment | kg ai/ha | CDM obs. % Control | CDM calc. % Control | TLB obs. % Control |
|---|---|---|---|---|
| None | | 0 | | 0 |
| Cmpd. E | 0.112 | 28 | | 30.9 |
| " | 0.225 | 35 | | 14.3 |
| " | 0.45 | 54 | | 57.1 |
| " | 0.9 | 77 | | 54.8 |
| Cmpd. A | 0.0125 | 63 | | 97.1 |
| Cmpd. A + Cmpd. E | 0.0125 + 0.112 | 55 | 73.4 | 94.8 |
| " | 0.0125 + 0.225 | 70 | 75.9 | 90 |
| " | 0.0125 + 0.45 | 69 | 83 | 93.8 |
| " | 0.0125 + 0.9 | 81 | 81 | 92.3 |
| Cmpd. A | 0.025 | 70 | | 96.7 |
| Cmpd. A + Cmpd. E | 0.025 + 0.112 | 60 | 78.4 | 97.6 |
| " | 0.025 + 0.225 | 71 | 80.5 | 97.1 |
| " | 0.025 + 0.45 | 81 | 86.2 | 92.9 |
| " | 0.025 + 0.9 | 85.8 | 93.1 | 95.2 |
| Cmpd. A | 0.05 | 82 | | 96.7 |
| Cmpd. A + Cmpd. E | 0.05 + 0.112 | 61 | 87 | 95.7 |
| " | 0.05 + 0.225 | 76 | 88.6 | 96.7 |
| " | 0.05 + 0.45 | 89 | 91.7 | 96.1 |
| " | 0.05 + 0.9 | 87.8 | 95.9 | 96.7 |
| Cmpd. A | 0.1 | 72 | | 97.1 |
| Cmpd. A + Cmpd. E | 0.1 + 0.112 | 71 | 79.8 | 98.6 |
| " | 0.1 + 0.225 | 87 | 81.8 | 97.6 |
| " | 0.1 + 0.45 | 89.6 | 87.1 | 99 |
| " | 0.1 + 0.9 | 93.6 | 93.6 | 96.7 |

EXAMPLE 3b

N-[3'-(1'-chloro-3'-methyl-2'-oxopentan)]-3,5-dichloro-4-methylbenzamide+Fosetyl-aluminum Combination Study–Second Application Rate Study As a result of the initial test, a second test was conducted against CDM with lower rates of N-[3'-(1'-chloro-3'-methyl-2'-oxopentan)]-3,5-dichloro-4-methylbenzamide. Results with the adjusted rates confirmed the previous test with the higher doses and indicated synergism at additional rates. There was very strong synergism with some rates. Ratios were from 1:2.25 to 1:36. The results are reported in Table 3b. Specific ratios where synergism was observed were 1:2.25, 1:4.5, 1:9, 1:18 and 1:36.

TABLE 3b

Control of CDM

| Treatment | kg ai/ha | CDM obs. % Control | CDM calc. % Control |
|---|---|---|---|
| None | | 0 | |
| Cmpd. E | 0.225 | 14 | |
| Cmpd. E | 0.45 | 33 | |
| Cmpd. E | 0.9 | 41 | |
| Cmpd. A | 0.006 | 22 | |
| Cmpd. A + Cmpd. E | 0.006 + 0.225 | 26 | 32.9 |
| Cmpd. A + Cmpd. E | 0.006 + 0.45 | 49 | 47.7 |
| Cmpd. A + Cmpd. E | 0.006 + 0.9 | 54 | 54 |
| Cmpd. A | 0.025 | 14 | |
| Cmpd. A + Cmpd. E | 0.025 + 0.225 | 45 | 26 |
| Cmpd. A + Cmpd. E | 0.025 + 0.45 | 51 | 42.4 |
| Cmpd. A + Cmpd. E | 0.025 + 0.9 | 57 | 49.3 |
| Cmpd. A | 0.1 | 22 | |
| Cmpd. A + Cmpd.E | 0.1 + 0.225 | 47 | 32.9 |
| Cmpd. A + Cmpd. E | 0.1 + 0.45 | 48 | 47.7 |
| Cmpd. A + Cmpd.E | 0.1 + 0.9 | 60 | 54 |

EXAMPLE 4

N-[3'-(1'-chloro-3'-methyl-2'-oxopentan)]-3,5-dichloro-4-methylbenzamide (Compound A)+Propamocarb (Compound F) Tests Against TLB and CDM Cucumber downy mildew and tomato late blight were effectively controlled with different combinations of N-[3'-(1'-chloro-3'-methyl-2'-oxopentan)]-3,5-dichloro-4-methylbenzamide and propamocarb.

Three week old Patio variety tomato and Busch Champion cucumber plants were sprayed with the fungicide rates listed in Tables 4a and 4b. One day following application, the plants were inoculated with spore 30–40×$10^4$ spores/ml suspensions of the respective diseases. The plants were incubated in mist cabinets for twenty-four hours and then placed in control temperature chambers for the duration of the experiment.

Visual assessments of disease infection was conducted and the transformed to percent control values. The data in Tables 4a and 4b suggest strong levels of synergism with the combinations. Ratios of N-[3'-(1'-chloro-3'-methyl-2'-oxopentan)]-3,5-dichloro-4-methylbenzamide to propamocarb ranged from 1:1 to 1:42. Synergism was seen at the ratios: 1:42, 1:21, 1:10.5, 1:5, 1:2.5 and 1:1.

TABLE 4a

Tomato Late Blight Control

| Treatment | Kg ai/ha | % Control Observed | % Control Calculated |
|---|---|---|---|
| Cmpd. F | 0.063 | 0 | |
| | 0.125 | 3 | |
| | 0.25 | 17 | |
| Cmpd. A | 0.006 | 23 | |
| | 0.012 | 20 | |
| | 0.025 | 36 | |
| Cmpd. A + Cmpd. F | 0.006 + 0.063 | 31 | 23 |
| | 0.006 + 0.125 | 37 | 27 |
| | 0.006 + 0.25 | 60 | 36 |
| Cmpd. A + Cmpd. F | 0.012 + 0.063 | 42 | 20 |
| | 0.012 + 0.125 | 34 | 22 |
| | 0.012 + 0.25 | 47 | 34 |
| Cmpd. A + Cmpd. F | 0.025 + 0.063 | 37 | 36 |
| | 0.025 + 0.125 | 50 | 38 |
| | 0.025 + 0.25 | 54 | 47 |

TABLE 4b

Cucumber Downy Mildew Control

| Treatment | Kg ai/ha | % Control Observed | % Control Calculated |
|---|---|---|---|
| Cmpd. F | 0.063 | 9 | |
| | 0.125 | 0 | |
| | 0.25 | 27 | |
| Cmpd. A | 0.006 | 56 | |
| | 0.012 | 33 | |
| | 0.025 | 45 | |
| Cmpd. A + Cmpd. F | 0.006 + 0.063 | 66 | 60 |
| | 0.006 + 0.125 | 67 | 56 |
| | 0.006 + 0.25 | 67 | 55 |
| Cmpd. A + Cmpd. F | 0.012 + 0.063 | 57 | 39 |
| | 0.012 + 0.125 | 47 | 33 |
| | 0.012 + 0.25 | 42 | 51 |
| Cmpd. A + Cmpd. F | 0.025 + 0.063 | 77 | 50 |
| | 0.025 + 0.125 | 82 | 45 |
| | 0.025 + 0.25 | 86 | 60 |

EXAMPLE 5a

N-[3'-(1'-chloro-3'-methyl-2'-oxopentan)]-3,5-dichloro-4-methylbenzamide (Compound A)+Folpet (Compound G) Tests Against CDM The results in the accompanying Table 5a are for N-[3'-(1'-chloro-3'-methyl-2'-oxopentan)]-3,5-dichloro-4-methylbenzamide and folpet. The test was conducted as using the standard protocol (Example 3a) for cucumber downy mildew. Treatments were evaluated as a 3-day residual application.

Synergism was observed at the following ratios of N-[3'-(1'-chloro-3'-methyl-2'-oxopentan)]-3,5-dichloro-4-methylbenzamide to folpet for CDM disease: 1:4.5, 1:9 and 1:18. The results are reported in Table 5a.

TABLE 5a

Cucumber Downy Mildew Control

| Treatment | Kg ai/ha | Number of Infection Sites | % Control Observed | % Control Calculated |
|---|---|---|---|---|
| Cmpd. G | 0.113 | 16 | 28.8 | |
| | 0.225 | 22.2 | 0 | |
| | 0.45 | 19.2 | 8.5 | |
| Cmpd. A | 0.025 | 5.4 | 74.3 | |
| | 0.05 | 3.2 | 84.8 | |
| | 0.1 | 0.4 | 98.1 | |
| Cmpd. A + | 0.025 + 0.225 | 3.6 | 82.9 | 74.3 |
| Cmpd. G | 0.025 + 0.45 | 2.2 | 89.5 | 76.5 |
| Cmpd. A + | 0.05 + 0.225 | 2.2 | 89.5 | 84.8 |
| Cmpd. G | 0.05 + 0.45 | 2.2 | 89.5 | 84.8 |

EXAMPLE 5b

N-[3'-(1'chloro-3'-methyl-2'-oxopentan)]-3,5-dichloro-4-methylbenzamide (Compound A)+Folpet (Compound G) Tests Against PLB Three to four week old potato seedlings were sprayed with a series of doses of folpet and N-[3'-(1'-chloro-3'-methyl-2'-oxopentan)]-3,5-dichloro-4-methylbenzamide. Individual treatments and combination treatments were compared for biological efficacy against *Phytophthora infestans* on potatoes (PLB). Fungicide solutions were sprayed and inoculated one day after the application. Inoculation was completed with a spore suspension of 30–40×$10^4$ spores/ml. The plants were placed in a misting cabinet for 24 hours Following the infection period, plants were placed in a constant temperature chamber for the duration.

One day following application, the plants were inoculated with spore suspensions of the respective diseases. The plants were incubated in mist cabinets for twenty-four hours and then placed in control temperature chambers for the duration of the experiment.

Disease pressure was very high in this test as is evidenced by the exceptionally low level of control expressed by the individual treatment. However the combinations were more active than either of the fungicides used alone.

N-[3'-(1'-chloro-3'-methyl-2'-oxopentan)]-3,5-dichloro-4-methylbenzamide and folpet at ratios of 1:2.25, 1:4.5 and 1:9 exhibited synergism in this test. The results are reported in Table 5b.

TABLE 5b

Potato Late Blight Control

| Treatment | Kg ai/ha | % Control Observed | % Control Calculated |
|---|---|---|---|
| Cmpd. G | 0.225 | 0 | |
| | 0.45 | 3.5 | |
| Cmpd. A | 0.05 | 12 | |
| | 0.10 | 16 | |
| Cmpd. A + Cmpd. G | 0.05 + 0.225 | 32 | 12 |
| | 0.05 + 0.45 | 20 | 15 |
| Cmpd. A + Cmpd. G | 0.10 + 0.225 | 21 | |
| | 0.10 + 0.45 | 39 | 19 |

EXAMPLE 6a

N-[3'-(1'-chloro-3'-methyl-2'-oxopentan)]-3,5-dichloro-4-methylbenzamide (Compound A)+Fluazinam (Compound H) Test Against TLB The results in the accompanying Table 6a are for N-[3'-(1'-chloro-3'-methyl-2'-oxopentan)]-3,5-dichloro-4- methylbenzamide and fluazinam against TLB. The test was conducted as using the standard protocol (Example 3a) for tomato late blight. Treatments were applied as one day protectant applications.

Synergism was observed at the 1:5 ratio of N-[3'-(1'-chloro-3'-methyl-2'-oxopentan)]-3,5-dichloro-4-methylbenzamide to fluazinam. The results are reported in Table 6a.

TABLE 6a

Tomato Late Blight Control

| Treatment | Kg ai/ha | % Infection | % Control Observed | % Control Calculated |
|---|---|---|---|---|
| Cmpd. H | 0.125 | 64 | 20 | |
| Cmpd. A | 0.025 | 13.2 | 84 | |
| Cmpd. A + Cmpd. H | 0.025 + 0.125 | 6.2 | 92 | 87.6 |

EXAMPLE 6b

N-[3'-(1'-chloro-3'-methyl-2'-oxopentan)]-3,5-dichloro-4-methylbenzamide (Compound A) +Fluazinam (Compound H) Test Against GDM An example of synergism was observed with fluazinam in a test against grape downy mildew, *Plasmopara viticola.*

Tissue culture produced from Delaware grapes were sprayed with the fungicides. Inoculation with grape downy mildew (GDM) spores having a concentration of 40,000 spores ml was conducted 1 day after the application. Plants were placed in a mist chamber for 24 hrs and then moved to a control temperature chamber for the remainder of the test period. The results are reported in Table 6b.

TABLE 6b

Grape Downy Mildew Control

| Treatment | Kg ai/ha | % Control Observed | % Control Calculated |
|---|---|---|---|
| Cmpd. H | 0.006 | 52 | |
| Cmpd. A | 0.006 | 22 | |
| Cmpd. A + Cmpd. H | 0.006 + 0.006 | 76 | |

It is to be understood that changes and variations in this invention may be made without departing from the spirit and scope of this invention as defined by the appended claims.

We claim:

1. A fungicidal composition comprising synergistic fungicidally effective amounts of (a) a first fungicidally active compound which is N-[3'-(1'-chloro-3'-methyl-2'-oxopentan)]-3,5-dichloro-4-methylbenzamide, (b) a second fungicidally active compound,compound which is the potassium salt of phosphorous acid, and (c) an agronomically acceptable carrier.

2. A method for controlling phytopathogenic fungi on a plant comprising the application of a synergistic fungicidally effective amount of the composition of claim 1.

3. The method of claim 2 wherein the phytopathogenic fungi belong to the class Oomycetes and are of the genera Phytophthora, Plasmopara, Peronospora, Albugo or Pseudoperonospora.

4. The method of claim 2 wherein the plant is a potato plant, a tomato plant, a grape plant or a cucumber plant.

5. The method of claim 2 wherein the amounts of the first and second fungicidally active compounds applied comprise from 2 parts by weight to 90 parts by weight of the first fungicidally active compound and from 10 parts by weight to 98 parts by weight of the second fungicidally active compound per 100 parts by weight of the combined amount of the first and second fungicidally active compounds.

* * * * *